United States Patent [19]

Brown

[11] Patent Number: 4,718,909

[45] Date of Patent: Jan. 12, 1988

[54] METHOD AND APPARATUS FOR CEMENTING A FEMORAL STEM PROSTHESIS WITHIN A FEMORAL CANAL

[76] Inventor: Byron L. Brown, 2315 Hendricks, Fort Smith, Ark. 72903

[21] Appl. No.: 755,600

[22] Filed: Jul. 16, 1985

[51] Int. Cl.$^4$ ............................................. A61F 2/28
[52] U.S. Cl. ...................................................... 623/16
[58] Field of Search ................................. 623/16–23; 128/303 R

[56] References Cited

U.S. PATENT DOCUMENTS

| 4,065,817 | 1/1978 | Branemark et al. | 623/18 |
| 4,357,716 | 11/1982 | Brown | 623/23 |
| 4,404,692 | 9/1983 | Effekhar | 623/22 |

FOREIGN PATENT DOCUMENTS

| 1409053 | 10/1975 | United Kingdom | 623/22 |
| 2104391 | 3/1983 | United Kingdom | 623/22 |

Primary Examiner—Richard J. Apley
Assistant Examiner—David J. Isabella
Attorney, Agent, or Firm—Sigalos & Levine

[57] ABSTRACT

Apparatus and method for positioning a prosthesis stem in a femoral canal such that a spacing exists everywhere between the prosthesis stem and the cortical bone of the femur and then filling the space between the stem and cortical bone with cement to hold the stem in the femoral canal.

6 Claims, 8 Drawing Figures

4,718,909

METHOD AND APPARATUS FOR CEMENTING A FEMORAL STEM PROSTHESIS WITHIN A FEMORAL CANAL

BACKGROUND OF THE INVENTION

The present invention relates to a method and apparatus for cementing a femoral stem hip prosthesis in a femoral canal with the use of a cement.

It is well known in the prior art to initiate total hip replacement as disclosed in U.S. Pat. No. 4,357,716, issued Nov. 9, 1982. In such cases, the femur is prepared to receive a femoral stem prosthesis which has a head, neck and stem. The proximal end of the femur is prepared by resecting the head and neck of the femur and then rasping or curetting the intramedullary canal in its proximal end and extending this process laterally and distally in the proximal shaft of the femur to accommodate a cement mass for support and fixation of the stem of a femoral prosthesis. Once the canal has been properly prepared by reaming and curettage, the distal canal is plugged, utilizing a bone plug obtained from the femoral head or formed in any other of the well known alternate methods. In any case, the plug effectively seals off the canal to prevent excessive penetration of cement below the tip of the stem of the prosthesis. Positioning of the prosthesis stem in the femoral canal and the relationship of the head and neck of the prosthesis with the shaft of the femur is important and is related in part to the position of the distal end of the femoral stem as well as the position of the proximal end of the prosthesis stem in the intertrochanteric area.

As described in U.S. Pat. No. 4,357,716, a fixed jig holds the prosthesis in fixed relationship to the femur thus eliminating motion of the prosthesis during the time that the pressurized cement is applied about the prosthesis stem in the femoral canal and the pressure is maintained until the cement hardens.

It has been found in all prior art methods of inserting the prosthesis stem in the femoral canal that, because there are such a variable number, shapes and sizes of femoral stems, it is difficult to place the trial femoral stem prosthesis into the femoral canal unless the distal tip of the prosthesis stem touches the cortical bone anteriorly or posteriorly and in a few instances perhaps medially or laterally. The touching of the cortical bone by the distal end of the stem is believed to be detrimental, however, inasmuch as it creates a pressure point on the cortical bone structure which may cause bone failure when the weight distribution of the patient is applied to the head of the femoral stem prosthesis and the weight transferred to the stem. These pressure points may either cause failure of the cortical bone or loosening of the cement holding the prosthesis stem in the femoral canal thereby creating problems for the patient. The cement should encircle the entire stem rather than having little or no cement at the tip of the prosthesis stem. However, this cannot be determined in the prior art prior to the cementing of the prosthesis stem in the canal itself. After the cementing has taken place in the prior art, the device can be x-rayed and the position of the stem determined with respect to the cortical bone structure of the femur. In such case, however, it is then too late to reposition the stem in a more desirable position.

Thus, it is an object of the present invention to correctly position the prosthesis in the femoral canal prior to cementing said stem in said canal such that a spacing exists everywhere between the stem of the prosthesis and the cortical bone of the femur and after this correct position has been determined, then the space between the stem and the cortical bone is filled with cement to hold the prosthesis in the femoral canal. It is also an object of the present invention to determine the correct spaced position of said stem in said canal prior to filling the space with the cement.

It is still another object of the present invention to support the prosthesis in the correct spaced position during filling of the space with cement and while the cement hardens.

It is yet another object of the present invention to place a spacing sleeve over the stem of the prosthesis and insert the prosthesis stem in the femoral canal with the sleeve holding the stem in the desired spaced relationship with the canal cortical bone.

It is another object of the present invention to attach a guide to the femur to support the prosthesis stem in its correct spaced position in the canal and then removing the stem from the canal whereby the spacing sleeve may be removed and the stem reinserted in said canal and held by said guide in its predetermined correct spaced position with the cortical bone.

It is still another object of the present invention to form the spacing sleeve of a cement permeable material whereby the stem is held in spaced relationship with the cortical bone of the femoral canal, said cement permeable material allowing flowable cement to pass therethrough and substantially surround the stem and contact substantially all of the cortical bone.

SUMMARY OF THE INVENTION

Thus the present invention relates to a method of cementing a femoral stem prosthesis within a femoral canal, said prosthesis having a head, neck and stem, said method comprising the steps of preparing the femoral canal for receiving the prosthesis, positioning said prosthesis in said canal prior to cementing said stem in said canal such that a spacing exists everywhere between the stem of the prosthesis and the cortical bone of said femur, and filling said space between said stem and said cortical bone with cement to hold said prosthesis in said femoral canal.

The present invention also relates to an apparatus for cementing a femoral stem prosthesis within a prepared femoral canal, said prosthesis having a head, neck and stem, said apparatus comprising means for positioning said stem in said canal such that a spacing exists everywhere between the stem of said prosthesis and the cortical bone of said femur, and means for filling said space with cement to hold said prosthesis in said femoral canal.

BRIEF DESCRIPTION OF THE DRAWINGS

These and other objects and advantages of the present invention will be disclosed in the course of the following specification, reference being had to the accompanying drawings in which.

DETAILED DESCRIPTION OF THE DRAWINGS

Figure 1:
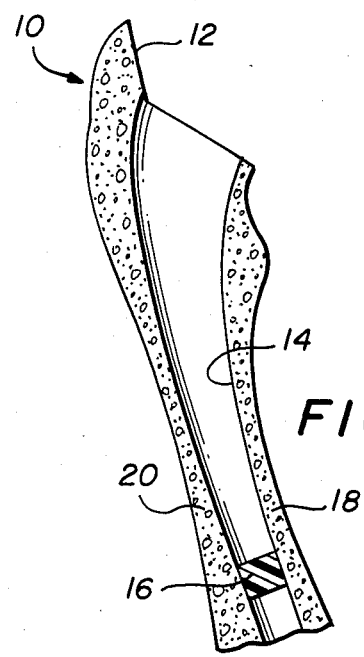
FIG. 1 is a partial illustration of a femur which has been prepared for receiving a femoral stem prosthesis.

FIG. 1 is a partial view of a femur 10 that has been properly prepared for the insertion of a femoral stem prosthesis. Thus, as can be seen in FIG. 1, the head and neck of the femur have been resected along line 12 and canal 14 has been prepared by curetting or rasping in the proximal end and this process has been extended well laterally and distally into the proximal shaft. Also as can be seen in FIG. 1, a bone plug or other well known type of plug 16 is used to plug the distal end of canal 14. Cortical bone 18 and 20 has been exposed on each side and surrounding canal 14. Femoral canal 14 is, of course, dried and otherwise prepared for receiving the femoral stem prosthesis.

Figure 2:
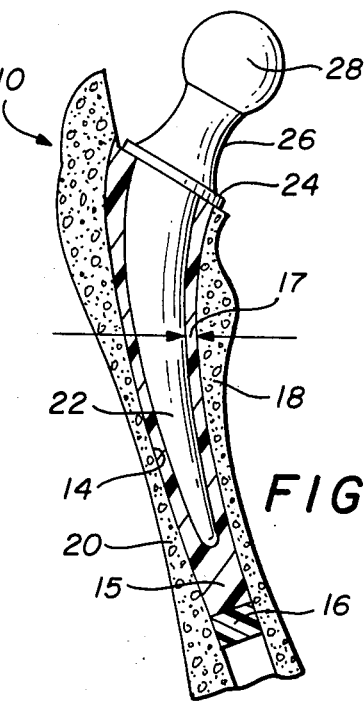
FIG. 2 is a partial drawing of a femur having the prosthesis properly positioned and cemented therein.

FIG. 2 illustrates the desired positioning of the prosthesis stem 22 in femoral canal 14 after the cement 15 has hardened. As will be noted in FIG. 2, the femoral stem prosthesis has a stem 22, shoulder 24, neck 26, and head 28. It will also be noted that the stem 22 is so positioned in the femoral canal 14 that a space 17 exists everywhere between it and the cortical bone 18 and 20. In this desired position, the cement 15 distributes the weight applied to head 28 by the person in which the prosthesis has been surgically implanted so that no one pressure point occurs on the cortical bone 18 or 20.

Figure 3:
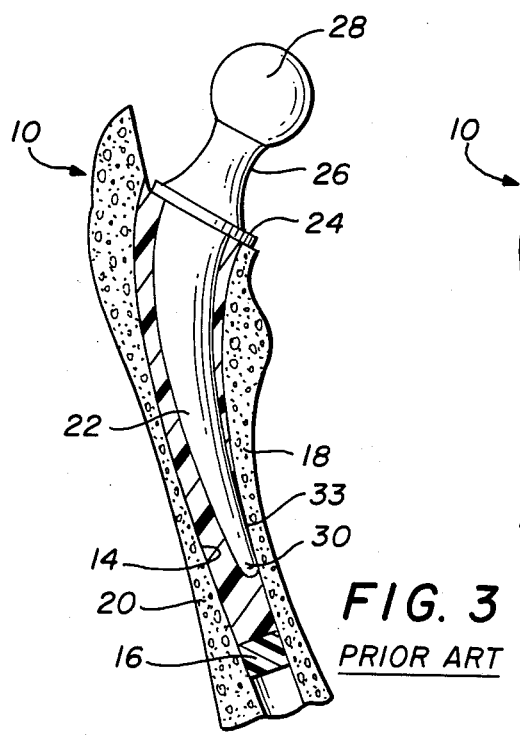
FIG. 3 is an illustration of a typical prior art cementing of a femoral stem prosthesis in the femoral canal such that the distal end of the prosthesis stem is touching the cortical bone and very little space exists between a portion of the stem and the cortical bone on one side thereof.

However, in the prior art methods of inserting the prosthesis stem 22 in the femoral canal 14, the exact position of the stem 22 with respect to the cortical bone 18 and 20 of the femur 10 cannot be determined until after the cement hardens and an x-ray is taken. Since the head 28 and neck 26 of the prosthesis must be positioned in anteversion, a relationship of the head and neck of the prosthesis with the shaft of the femur, the distal end 30 of the femoral stem 22 moves in canal 14 and may very well touch the cortical bone as shown at 32 in FIG. 3. Thus, there is little or no cement at point 32 between the stem 22 and cortical bone 18. This means that any weight applied by the patient to head 28 of the prosthesis is transmitted through stem 22 to distal end 30 of the stem 22 and pressure is applied at 32 to the cortical bone 18 thus concentrating the pressure in a localized area which may cause failure of cortical bone 18 at that point. If failure of cortical bone 18 does not occur, a weakening of the cement 15 may occur around the stem 22 because of the pressure at point 32 thus eventually allowing the stem 22 to become loose in the femoral canal 14.

Figure 4:
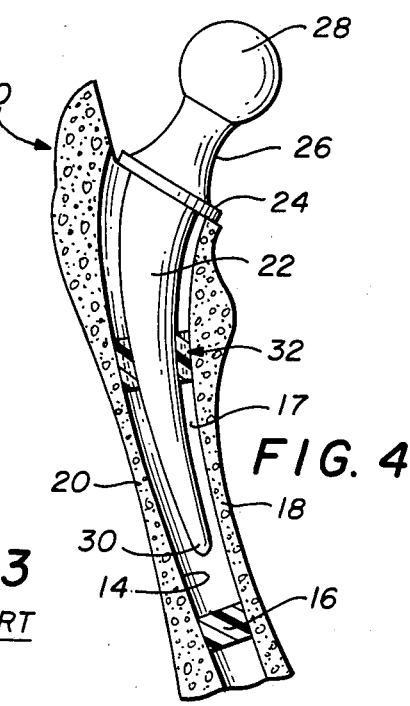
FIG. 4 illustrates the manner in which the present invention utilizes a spacing sleeve about the stem of the prosthesis to cause a spacing to exist everywhere between the stem of the prosthesis and the cortical bone of the femur.

FIG. 4 is an illustration of the method and apparatus of the present invention for positioning the prosthesis stem 22 in the femoral canal 14 prior to cementing the stem in the canal such that a spacing exists everywhere between the stem 22 of the prosthesis and the cortical bone 18 and 20 of the femur. Thus, as can be seen in FIG. 4, a spacing sleeve 32 is placed around stem 22 of the prosthesis which is then inserted in canal 14 and spacing sleeve 32 maintains a space 17 everywhere about stem 22 in canal 14. Thus, it will be seen that the distal end 30 of stem 22 is approximately centered in the canal 14 and a space exists everywhere around the stem 22 and distal end 30 of the stem 22 so that cement 15 can completely surround the stem 22 and fill the space 17 and make contact with the cortical bone 18 and 20.

Figure 5:
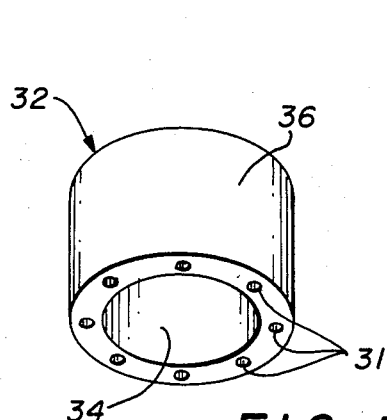
FIG. 5 is a perspective view of the spacing sleeve of the present invention which is used in FIG. 4 to substantially center the prosthesis stem in the femoral canal.

A typical spacing sleeve is illustrated in FIG. 5 and is shown to be cylindrical in shape; however, each sleeve 32 would conform to the outer surface of the femoral stem 22. In other words, the inner aspect 34 of sleeve 32 would fit the outer end of femoral stem 22 and the outer surface 36 of sleeve 32 would fill canal 14. The sleeve 32 would have longitudinally extending orifices 31 to allow moderate compressibility so as to allow some adjustment of the sleeve 32 and the stem 22 to the size of the canal 14 and is of sufficient length to properly place the femoral stem 22 and thus would not necessarily need to extend to the distal tip 30 of the femoral stem 22. For example, sleeve 32 could be located ½ to 1 inch from the distal end of prosthesis stem 22. It need have sufficient length only to maintain the stem 22 substantially centered in canal 14 with a space 17 everywhere between stem 22 and cortical bone 18 and 20. This sleeve could be made of any metal or plastic permitted for body use.

Figure 6:
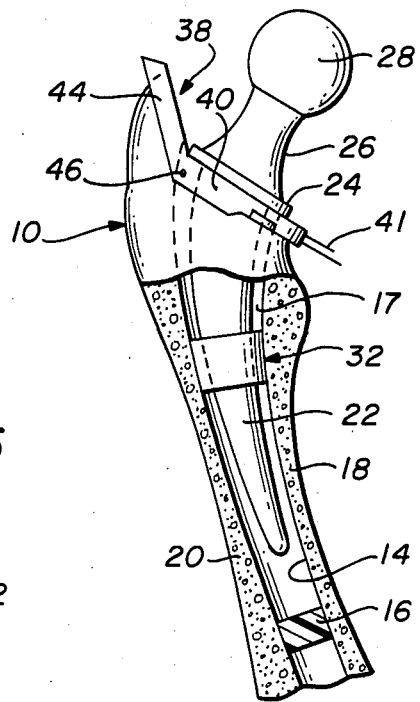
FIG. 6 illustrates the placement of a guide to remember the correct position of the stem and to support the prosthesis in said correct position after said spacing sleeve has been removed and which is rigidly attached to the femur.

Thus, once the stem 22 has been properly positioned in the femoral canal 14 by the use of the spacing sleeve 32 as illustrated in FIG. 4, a jig can be rigidly attached to the femur to "remember" the correct position of the stem 22 in the canal 14 as determined by spacing sleeve 32. Such a jig is illustrated in FIG. 6 and is actually a base guide 38 which is rigidly attached to the femur by use of pins 40 and 42 as disclosed in detail in U.S. Pat. No. 4,357,716. In addition, U.S. Pat. No. 4,357,716 also discloses the use of a separator-sealer, ceiling and lid clamp, all of which are rigidly attached to base guide 38 thus immobilizing the entire prosthesis including stem 22 in the correct position as determined by spacing sleeve 32 and illustrated in FIG. 6. The manner in which the separator-sealer, ceiling and lid clamp are attached to the base guide 38 as illustrated in U.S. Pat. No. 4,357,716 is incorporated herein by reference as if fully made a part hereof. Thus, once the stem 22 has been properly positioned by the spacing sleeve 32 and the base guide 38 rigidly mounted to the femur to "remember" the proper position of stem 22 and provide a support for the prosthesis in the correct position illustrated in FIG. 6, the prosthesis can then be removed without disturbing base guide 38 and the spacing sleeve 32 removed from the stem 22. The prosthesis can then be reinserted in the canal 14 and will be held in its proper "remembered" position by base guide 38 which will then maintain the prosthesis in the correct position so that stem 22 will not touch the cortical bone 18 or 20 and in fact maintain the space everywhere between stem 22 and cortical bone 18 and 20 of the femur 10. At this stage, the separator, ceiling and lid clamp can be reattached to the prosthesis head 28 and neck 26 as disclosed in U.S. Pat. No. 4,357,716 and a flowable or liquid cement 15 injected under pressure into the spacing about stem 22 which will then harden and will contact not only all of stem 22 but also all of the cortical bone 18 and 20 thus providing uniform distribution of the weight applied to head 28 of the prosthesis through stem 22 to cortical bone 18 and 20 through the cement 15.

Figure 7:
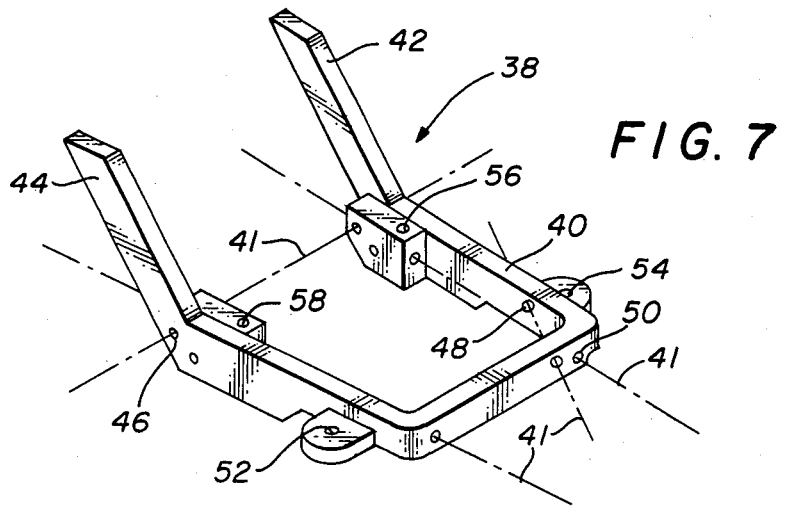
FIG. 7 is an isometric view of the base guide which remembers the correct position of said stem in said canal and which supports the prosthesis in its correct position after said spacing sleeve has been removed and which is rigidly attached to the femur.

The base guide 38 is illustrated in FIG. 7 and comprises a U-shaped frame 40 having upwardly extending wings 42 and 44. A plurality of orifices 46, 48 and 50 may be used for pins such as K wires or drill bits to rigidly attach the base guide 38 to the femur 10. In addition, orifices 52, 54, 56 and 58 may be used as disclosed in U.S. Pat. No. 4,357,716 to attach the ceiling and the lid clamp to the base guide 38 to allow the cement 15 to be injected in the space existing between stem 22 and cortical bone 18 and 20 as disclosed.

Figure 8:
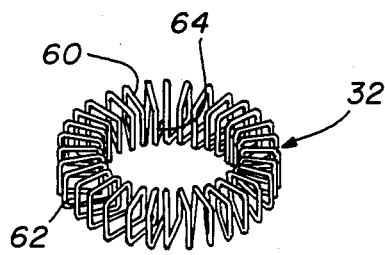
FIG. 8 is a perspective representation of an alternate form of spacing sleeve which is of cement permeable material such as a circular arranged coiled spring made of a resilient material that can be utilized in the femoral canal and thus can be allowed to remain in the femoral canal inasmuch as liquid or flowable cement can pass therethrough and substantially surround the stem and make contact with substantially all of the cortical bone of the femur.

After the cement 15 has set, the base guide 40 and its associated elements are removed and the prosthetic device as cemented in the femur 10 appears as shown in FIG. 8. It will be noted in this case that the cement 15 in canal 14 totally surrounds stem 22 of the prosthesis and fills space 17. The weight applied by the patient through ball or head 28 is transmitted to the stem 22 which in turn transmits the forces equally through cement 15 to the cortical bone 18 and 20.

FIG. 8 illustrates an alternative embodiment of the spacing sleeve 32 which is formed of a circular arrangement of coiled resilient material such as plastic 60 which, of course, has an outer edge 62 and an inner edge 64. The inner edge 64 fits against the prosthesis stem 22 while the outer edge 62 conforms itself to the shape of the femoral canal 14. By the use of this type of spacing sleeve 32, the sleeve is cement permeable whereby the stem 22 is held in spaced relationship with the cortical bone 18 and 20 of the femoral canal but the cement permeable material in the form of coil 60 allows a flowable cement 15 to pass therethrough and substantially surround and contact the stem 22 and contact substantially all of the cortical bone 18 and 20. Of course, any cement permeable type material could be used for sleeve 32 such as a porous material, lattice constructed material and the like so long as it is cement permeable and so long as it is made of a material such as metal or plastic which is permitted for body use and which will support stem 22 of the prosthesis. In this instance, the spacing sleeve 32 in the form of coiled resilient metal 60 does not have to be removed from the femoral canal 14 once the prosthesis stem 22 has been properly positioned therein and the base guide 38 and its associated components can be attached to the prosthesis and cement 15 introduced into the space 17 in the canal 14 between the stem 22 and the cortical bone 18 and 20. The cement can harden with the spacing sleeve 32 in place in this instance.

Thus, there has been disclosed a novel method and apparatus for cementing a femoral stem prosthesis in the femoral canal in such a way that there is a space existing everywhere between the stem of the prosthesis and the cortical bone of the femur thereby allowing any pressure applied to the femoral stem to be evenly distributed through the cement to the cortical bone structure of the femur. Not only does this allow for a stronger physical structure but also minimizes the chance for the stem of the prosthesis to become loose in the cement.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

I claim:

1. A method of cementing a femoral stem prosthesis within a femoral canal, said prosthesis having a head, neck and stem, said method comprising the steps of:
   a. preparing the femoral canal for receiving the prosthesis,
   b. placing a spacing sleeve over said stem of said prosthesis,
   c. inserting said stem in said femoral canal with said sleeve holding said stem in a correct spaced relationship with the canal cortical bone such that a spacing exists everywhere between the stem of said prosthesis and the cortical bone of said femur,
   d. attaching a guide to said femur to support said stem in said correctly spaced position in said canal,
   e. removing said stem from said canal,
   f. removing said spacing sleeve from said stem,
   g. replacing a stem in said canal supported by said guide such that said correct stem position is established and maintained by said guide, and
   h. filling said space between said stem and said cortical bone with cement to hold said prosthesis in said femoral canal.

2. A method as in claim 1 further including the step of forming said spacing sleeve of a metal permitted for body use.

3. A method as in claim 1 further comprising the step of forming said spacing sleeve of a plastic permitted for body use.

4. Apparatus for cementing a femoral stem prosthesis within a prepared femoral canal, said prosthesis having a head, neck and stem, said apparatus comprising:
   a. a spacing sleeve encircling at least a portion of said prosthesis stem to correctly position said stem in said canal such that a spacing exists everywhere between the stem of said prosthesis and the cortical bone of said femur,
   b. a guide attached to said femur for supporting said stem in said correct position as determined by said spacing sleeve and for remembering said correct spaced position of said stem when said stem is removed from said canal, said spacing sleeve is removed and said stem is replaced in said canal, and
   c. means for filling said space with cement to hold said prosthesis stem in said femoral canal in said spaced position.

5. Apparatus as in claim 4 wherein said spacing sleeve is formed of a metal permitted for body use.

6. Apparatus as in claim 4 wherein said spacing sleeve is formed of a plastic permitted for body use.

* * * * *